United States Patent [19]

Koot

[11] Patent Number: 4,713,065
[45] Date of Patent: Dec. 15, 1987

[54] URINE-RECEIVING SYSTEM

[75] Inventor: Hubertus H. M. Koot, Cuyk, Netherlands

[73] Assignee: Mandhy Products B.V. Cuyk, Netherlands

[21] Appl. No.: 869,877

[22] Filed: Jun. 3, 1986

[30] Foreign Application Priority Data

Mar. 13, 1986 [NL] Netherlands .......................... 8600656

[51] Int. Cl.$^4$ ................................................ A61F 5/44
[52] U.S. Cl. .................................... 604/329; 604/331; 604/402
[58] Field of Search ................................ 604/327–331, 604/346–350, 354–358, 378, 381, 393–402; 4/144.1–144.4

[56] References Cited

U.S. PATENT DOCUMENTS

| 2,104,423 | 1/1938 | Hughes | 604/397 |
| 3,349,768 | 10/1967 | Keane | 604/347 |
| 3,613,123 | 10/1971 | Langstrom | 604/347 |
| 4,202,058 | 5/1980 | Anderson | 604/347 |
| 4,246,901 | 1/1981 | Michaud | 604/329 |
| 4,270,539 | 6/1981 | Michaud | 604/347 |
| 4,610,675 | 9/1986 | Triunfol | 604/331 |

FOREIGN PATENT DOCUMENTS

| 0941477 | 1/1949 | France | 604/397 |
| 2148126 | 5/1985 | United Kingdom | 604/347 |

Primary Examiner—John D. Yasko
Assistant Examiner—Mario Costantino
Attorney, Agent, or Firm—John P. Snyder

[57] ABSTRACT

A urine incontinence device particularly for women is provided having an elongated urine receiving element made from elastic material. The receiving element is open on one side for receiving urine, and attached via a tube to a collection receptacle. The open side of the receiving element contains an inset body of moisture absorbing material. The inset body is provided with a peripheral edge portion which overlies the circumferential edge of the receiving element to separate the receiving element from a patient. The inset body has a plurality of protuberances which extend into receiving element to aid in pumping liquid to the collection receptacle upon movement of the legs of an associated patient to squeeze fluid from the inset body.

13 Claims, 4 Drawing Figures

URINE-RECEIVING SYSTEM

This invention relates to a urine-receiving system intended particularly for women, and consisting principally of an on one side open, oblong receiving element of elastic material of stable form with a drainage opening, a flexible drainage conduit joined to said opening and a collecting reservoir connected to said conduit.

There have already been in the past many proposals made to make urine-receiving systems suitable for women, whereby the problem arises that the urine may not remain in contact with the skin, since after some time this causes irritation. The urine-receiving systems known until now have not been able to solve this problem and are therefore never widely-adopted in practice.

The invention has for its aim to provide a system whereby the above-mentioned problem does not occur, which system is distinguished by an inset-body of moisture-absorbing material, such as cellulose material, to be placed in the receiving element.

The inset-body of moisture-absorbing material according to the invention seems contradictory to the receiving of urine in, and drainage thereof to, a collecting reservoir. The invention breaks through this contradiction in that it is based on the phenomenon that during movement of the body the inset-body is regularly "squeezed out". The urine so released disappears largely into the receiving element and thus into the collecting reservoir.

In order to improve the sealing towards the body, the inset-body is provided with a circumferential strip whereof the dimensions agree with those of the upper edge of the open side of the receiving element.

In this way the upper edge of the receiving body, which lies against the body of the patient, is completely closed off.

In order to facilitate the drainage of urinous liquid from the inset-body during the so-called "squeezing out", the inset-body is on the side facing away from the open side provided with one or more pumping members projecting into the receiving element. These pumping members in the form of protuberances leave some free space over in the receiving element, through which during squeezing out of the inset body, the urinous liquid can be more easily drained off.

It is preferable to fabricate each pumping member of the same moisture-absorbing material as that used for the inset body, and to cover the upper side of the inset body with a moisture-repellent yet permeable layer. This gives an "always dry" upper side, which strongly reduces the skin irritation.

The invention is further explained by reference to the description with figures, hereunder, of two embodiments.

Figure 3:
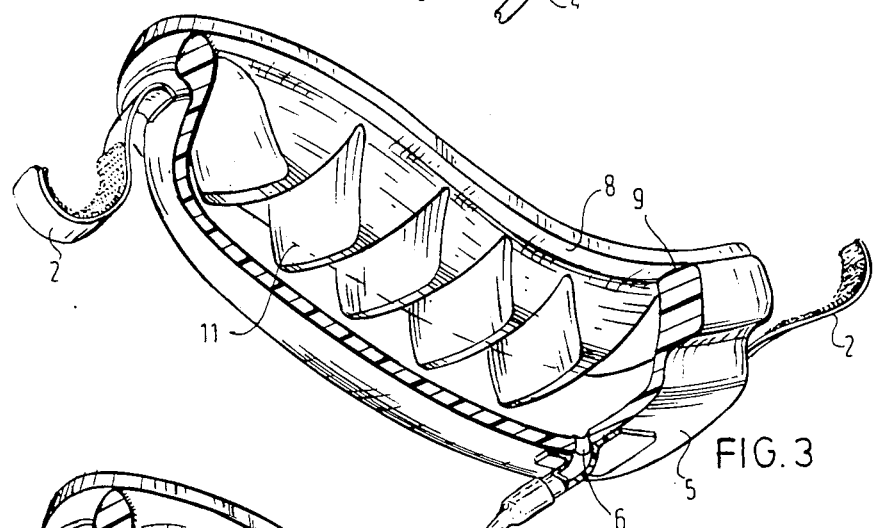
Figure 4:
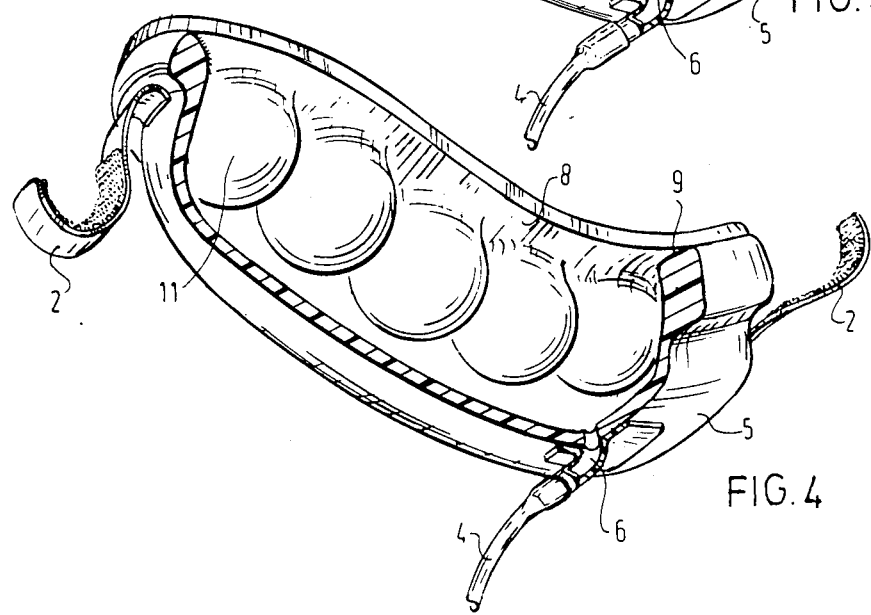

FIGS. 3 and 4 each show a perspective under-view, with the receiving element partly cut away, of one of two embodiments.

Figure 1:
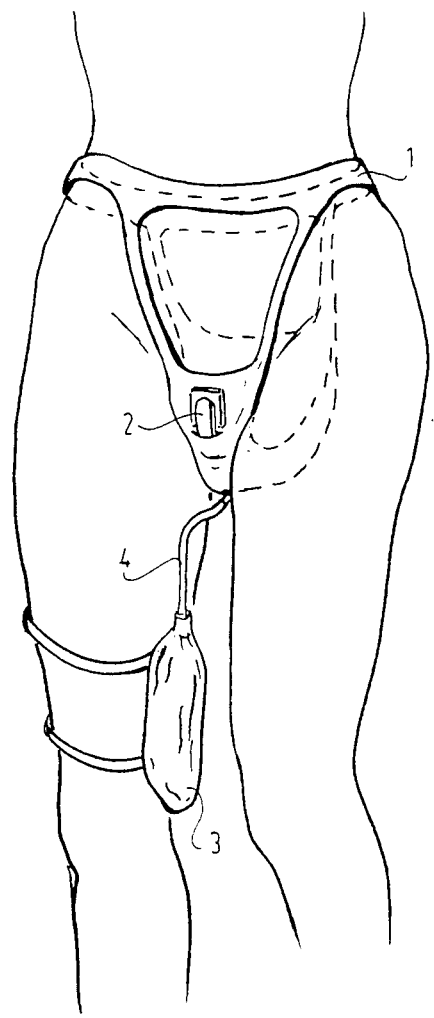
FIG. 1 shows a front view of a urine-receiving system for women, according to the invention.

In FIG. 1, the numeral 1 denotes a supporting band or girdle which can be fitted around the waist in any suitable manner. The girdle supports between the legs of the patient the urine-receiving system according to the invention, which is further explained below by reference to FIGS. 2 and 4. It consists of a, supported and carried by the girdle, receiving element, which can for example be fastened in the girdle by velcro strip 2, and to which there is connected collecting reservoir 3 to be fastened to the leg, which reservoir is connected via flexible conduit 4 to the urine-receiving system.

Figure 2:
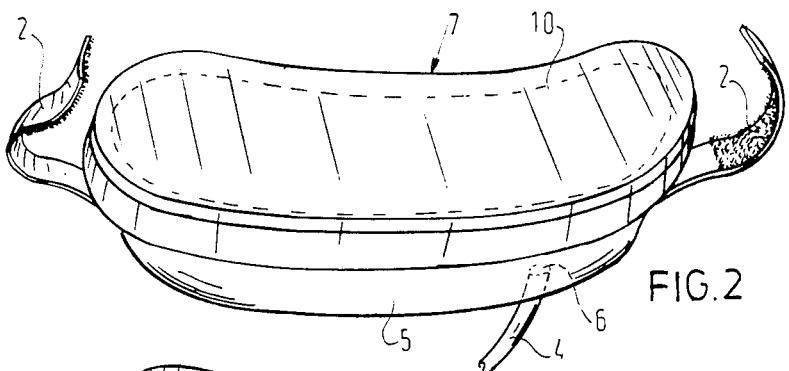
FIG. 2 shows a perspective top view of an embodiment applicable in the system of FIG. 1.

In FIGS. 2 to 4 inclusive, the receiving element is shown in further detail. Receiving element 5 is made with velcro-tape 2 at front and rear, for fastening to girdle 1. At the bottom there is situated drainage opening 6, to which flexible tube 4 is connected. This tube 4 may be integral with the receiving element, but may also be detachably connected to it.

In accordance with the invention, the oblong bowl-like receiving element 5 is provided at the open upper side with inset-body 7 which is made from suitable moisture-absorbing material. This can be cellulose stuff, for example. As can be seen in FIGS. 3 and 4, inset-body 5 is made with an encompassing edge-strip 8 which corresponds dimensionally with upper edge 9 of receiving element 7. From the figures it is clearly apparent that owing to this encompassing edgestrip 8, bowl-like receiving element 5 does not come into direct contact with the patient's skin. By preference, the upper side of inset-body 7 is covered with moisture-repellant yet permeable layer 10, which covers the entire upper side of the insert-body. The upper side can moreover have any required form in relief, so that it can be adapted in the most suitable way to body size and build. It should be remarked here that receiving element 5 is fabricated from a flexible but relatively stably-shaped material, such that inset-body 7 is adequately supported but that little inconvenience is caused to the patient.

In accordance with a further characteristic of the invention, inset-body 7 is provided on the side opposite to the open top side with one or more pumping means, here taking the form of protuberances 11. In FIG. 3 the protuberances have a prismatic form and are triangular in cross-section, such that triangular spaces are left over between the protuberances. The protuberances are preferably of the same material as inset-body 7, and are thus moisture-absorbing. Since during walking motion or other movements of the patient relatively form-stable receiving element 5 is in a sideways sense alternately pressed inwards and released, a pumping effect occurs upon members 11, by which urinous fluid is repeatedly pressed out therefrom, which fluid gathers in the spaces between members or protuberances 11, and which can subsequently be drained rapidly under the influence of gravity via drainage opening 6 and drainage conduit 4.

FIG. 4 shows a variant of the pumping members or protuberances, which are here principally spherical.

Finally it should be remarked that the inset body can be made as a disposable element, which means that it is simple for the patient to clean herself regularly and thereby prevent irritation.

The invention is not limited to the above-described embodiments. Thus within the framework of the invention any inset-body, without or with arbitrarily-shaped protuberances, is possible.

I claim:

1. A urine-receiving system intended particularly for women comprising receiving means formed of elastic material of stable form, said receiving means having a cavity therein and a receiving opening in one side thereof for receiving urine into said cavity said receiving opening having an edge extending around its periphery, said receiving means having a drainage opening therein in communication with said cavity, a flexible drainage conduit connected to said drainage opening, a collecting reservoir connected to said drainage conduit for receiving fluid from said drainage opening, and an inset-body disposed within and enclosing said receiving opening in its entirety, said inset-body being formed of an integral body of moisture absorbing material so dimensioned as to be readily inserted into and removed from said receiving opening, said inset-body having a peripheral edge portion disposed in overlying relationship to the edge of the receiving opening so that the inset-body contacts an associated patient and spaces the receiving means from the patient when in use.

2. A system as defined in claim 1 wherein the inset-body has an upper surface facing away from said receiving means, said upper surface being covered with a layer of moisture-repellent yet permeable material.

3. A urine-receiving system intended particularly for women comprising receiving means formed of elastic material of stable form, said receiving means having walls and being hollow to define a cavity, said receiving means having a receiving opening through one side thereof for receiving urine into the hollow interior of the receiving means, said receiving means having a drainage opening therein in communication with the hollow interior of the receiving means, a flexible drainage conduit connected to said drainage opening, a collecting reservoir connected to said drainage conduit for receiving fluid from said drainage opening, an inset-body formed of moisture absorbing material supported at said drainage opening for directly receiving urine, said inset-body having pumping means extending into the hollow interior of the receiving means and defining material-free space within the cavity between the cavity walls and the inset-body to drain fluid from the inset-body to said drainage opening when the pumping means is alternately pressed inwards and released by the receiving means upon movement of the legs of a patient.

4. A system as defined in claim 3 wherein said pumping means comprises a plurality of spaced protuberances formed of the same material as the inset-body.

5. A system as defined in claim 4 wherein said protuberances have a tapered cross-sectional configuration.

6. A system as defined in claim 4 wherein said protuberances have a curved cross-sectional configuration.

7. A system as defined in claim 3 wherein said inset-body has a peripheral edge portion covering adjacent side portions of the receiving means so that the inset-body is adapted to contact a patient's skin and spaces the receiving means from the patient's skin.

8. A system as defined in claim 3 wherein the inset-body has an upper surface facing away from said receiving means, said upper surface being covered with a layer of moisture-repellent yet permeable material.

9. A urine-receiving system intended particularly for women comprising oblong receiving means formed of elastic material of stable form, said receiving means defining a cavity therein and a receiving opening in one side thereof for receiving urine into said cavity, said receiving means having a drainage opening at another side thereof opposite to said one side of the receiving means and being in communication with said cavity, a flexible drainage conduit connected to said drainage opening, a collecting reservoir connected to said drainage conduit for receiving fluid from said drainage opening, an inset-body formed of moisture absorbing material for directly receiving urine, said inset-body being supported by said receiving means and overlying said receiving opening, said inset-body having pumping means extending into said cavity including a plurality of integral portions extending within said receiving element and having spaced outer surfaces which provide material-free space within the receiving element and in communication with said drainage opening, said receiving means having wall portions engageable with said integral portions of the inset-body for alternately pressing inwardly and releasing said integral portions upon movement of the legs of an associated patient to squeeze fluid from the inset-body and drain such fluid through said material-free space to the drainage opening.

10. A system as defined in claim 9 wherein said integral portions have a tapered cross-sectional configuration.

11. A system as defined in claim 9 wherein said integral portions have a curved cross-sectional configuration.

12. A system as defined in claim 9 wherein said inset-body has a circumferential edge portion covering adjacent side portions the receiving means so that the inset-body is adapted to contact a patient's skin and spaces the receiving means from the patient's skin.

13. A system as defined in claim 9 wherein the inset-body has an upper surface facing away from said receiving means, said upper surface being covered with a layer of moisture-repellent yet permeable material.

* * * * *